United States Patent
Ong et al.

(10) Patent No.: US 9,150,452 B2
(45) Date of Patent: Oct. 6, 2015

(54) METHOD FOR MANUFACTURING A CEMENTITIOUS COMPOSITION

(71) Applicant: Construction Research & Technology GmbH, Trostberg (DE)

(72) Inventors: Frank Shaode Ong, Solon, OH (US); Stefan Müssig, Sagamore Hills, OH (US); Darren Gambatesa, Chagrin Falls, OH (US); James C. Smith, Cuyahoga Falls, OH (US); Raymond Fete, Aurora, OH (US); Rick Paponetti, Bedford, OH (US); Mark A. Bury, Middleburg Heights, OH (US)

(73) Assignee: Construction Research & Technology, GmbH, Trostberg (DE)

( * ) Notice: Subject to any disclaimer, the term of this patent is extended or adjusted under 35 U.S.C. 154(b) by 240 days.

(21) Appl. No.: 13/836,495

(22) Filed: Mar. 15, 2013

(65) Prior Publication Data

US 2014/0107238 A1    Apr. 17, 2014

Related U.S. Application Data

(60) Provisional application No. 61/635,562, filed on Apr. 19, 2012, provisional application No. 61/695,134, filed on Aug. 30, 2012.

(51) Int. Cl.

| | |
|---|---|
| *C04B 16/08* | (2006.01) |
| *C04B 28/02* | (2006.01) |
| *C04B 38/08* | (2006.01) |
| *C04B 40/00* | (2006.01) |
| *C08L 101/14* | (2006.01) |
| *A61L 15/60* | (2006.01) |
| *C04B 111/20* | (2006.01) |

(52) U.S. Cl.
CPC .............. *C04B 16/085* (2013.01); *A61L 15/60* (2013.01); *C04B 28/02* (2013.01); *C04B 38/085* (2013.01); *C04B 40/0039* (2013.01); *C08L 101/14* (2013.01); *C04B 2111/29* (2013.01)

(58) Field of Classification Search
CPC .... C04B 16/085; C04B 28/02; C04B 38/085; C04B 40/0039; C04B 2111/29; C08L 101/14
See application file for complete search history.

(56) References Cited

U.S. PATENT DOCUMENTS

| | | | |
|---|---|---|---|
| 4,005,033 A * | 1/1977 | Georgeau et al. | 521/59 |
| 4,057,526 A | 11/1977 | De Rook | |
| 4,513,106 A * | 4/1985 | Edgren et al. | 521/58 |
| 4,778,829 A | 10/1988 | Ichimura et al. | |
| 6,084,011 A | 7/2000 | Lucero et al. | |
| 7,543,642 B2 | 6/2009 | Reddy et al. | |
| 2005/0274285 A1 | 12/2005 | Christensen et al. | |
| 2005/0284340 A1 | 12/2005 | Vickers, Jr. et al. | |
| 2007/0098973 A1 | 5/2007 | Wagner et al. | |
| 2007/0137528 A1 | 6/2007 | Le Roy-Delage et al. | |
| 2009/0093588 A1 | 4/2009 | Akutsu et al. | |
| 2009/0149559 A1 * | 6/2009 | Masuda et al. | 521/56 |

FOREIGN PATENT DOCUMENTS

| | | |
|---|---|---|
| DE | 1 961 390 | 6/1971 |
| DE | 10 2006 009 842 A1 | 9/2007 |
| EP | 0 320 473 A1 | 6/1989 |
| EP | 0 950 699 A1 | 10/1999 |
| FR | 2072897 | 9/1971 |
| GB | 2 347 413 A | 9/2000 |
| JP | 2005-254213 A | 9/2000 |
| WO | WO 03/051793 A2 | 6/2003 |
| WO | WO 2004/056549 A1 | 7/2004 |
| WO | WO 2006/133855 A2 | 12/2006 |
| WO | WO 2009/040359 A1 | 4/2009 |
| WO | WO 2010/070987 A1 | 6/2010 |

OTHER PUBLICATIONS

PCT/EP2013/058155—International Search Report, Sep. 2, 2013.
PCT/EP2013/058155—International Written Opinion, Sep. 2, 2013.
PCT/EP2013/037455—International Search Report, Sep. 2, 2013.
PCT/EP2013/037455—International Written Opinion, Sep. 2, 2013.
PCT/EP2013/058156—International Search Report, Sep. 2, 2013.
PCT/EP2013/058156—International Written Opinion, Sep. 2, 2013.
Moennig, et al., "Water saturated super-absorbent polymers used in high strength concrete", Otto-Graf-Journal: Annual Journal on Research and Testing of Materials, Jan. 1, 2005, vol. 16, pp. 193-202, Stuttgard, Germany.

* cited by examiner

*Primary Examiner* — Irina S Zemel
(74) *Attorney, Agent, or Firm* — Curatolo Sidoti Co., LPA; Joseph G. Curatolo; Vincent A. Cortese

(57) ABSTRACT

A method of expanding expandable polymeric microspheres including contacting an aqueous slurry including unexpanded, expandable polymeric microspheres with steam in-situ during manufacture of a cementitious composition or article, wherein the aqueous slurry optionally further includes an admixture therefor. A method of manufacturing a cementitious composition or article includes: (i) contacting an aqueous slurry of unexpanded, expandable polymeric microspheres with steam proximate to and/or during said manufacturing of the cementitious composition to create expanded polymeric microspheres; (ii) pre-wetting the expanded polymeric microspheres; and (iii) mixing the pre-wetted, expanded polymeric microspheres with cement and water to form the cementitious composition, wherein the aqueous slurry optionally further comprises an admixture therefor.

17 Claims, 5 Drawing Sheets

METHOD FOR MANUFACTURING A CEMENTITIOUS COMPOSITION

This application claims the benefit of the filing date under 35 U.S.C. §119(e) from U.S. Provisional Application Patent Ser. No. 61/635,562 filed on Apr. 19, 2012 and Ser. No. 61/695,134 filed on Aug. 30, 2012.

Provided is a method of expanding expandable polymeric microspheres and a method of manufacturing a cementitious composition including expanding expandable polymeric microspheres and mixing the expanded, expandable polymeric microspheres with cement and water to form a cementitious composition.

Freeze-thaw cycles can be extremely damaging to water-saturated hardened cementitious compositions, such as concrete. The best known technique to prevent or reduce the damage done is the incorporation in the composition of microscopically fine pores or voids. The pores or voids function as internal expansion chambers and can therefore protect the composition from freeze-thaw damage by relieving changes in hydraulic pressure caused by freeze-thaw cycling. A conventional method used for producing such voids in cementitious compositions is by introducing air-entraining agents into the compositions, which stabilize tiny bubbles of air that are entrapped in the composition during mixing.

Unfortunately, this approach of producing air voids in cementitious compositions is plagued by a number of production and placement issues, some of which are the following:

Air Content: Changes in air content of the cementitious composition can result in a composition with poor resistance to freeze-thaw damage if the air content drops with time or reduce the compressive strength of the composition if the air content increases with time. Examples are pumping a cementitious composition (decreasing air content by compression), job-site addition of a superplasticizer (often elevates air content or destabilizes the air void system), and interaction of specific admixtures with the air-entraining surfactant (that could increase or decrease air content).

Air Void Stabilization: The inability to stabilize air bubbles may be caused by the presence of materials that adsorb the stabilizing surfactant, i.e., fly ash having high surface area carbon or insufficient water for the surfactant to work properly, i.e, low slump concrete.

Air Void Characteristics: Formation of bubbles that are too large to provide resistance to freezing and thawing damage may be the result of poor quality or poorly graded aggregates, use of other admixtures that destabilize the bubbles, etc. Such voids are often unstable and tend to float to the surface of the fresh concrete.

Overfinishing: Removal of air by overfinishing, removes air from the surface of the concrete, typically resulting in distress by scaling of the detrained zone of cement paste adjacent to the overfinished surface.

The generation and stabilization of air at the time of mixing and ensuring it remains at the appropriate amount and air void size until the cementitious composition hardens remain the largest day-to-day challenges for the cementitious composition producer in North America. The air content and the characteristics of the air void system entrained into the cementitious composition cannot be controlled by direct quantitative means, but only indirectly through the amount and/or type of air-entraining agent added to the composition. Factors such as the composition and particle shape of the aggregates, the type and quantity of cement in the mix, the consistency of the cementitious composition, the type of mixer used, the mixing time, and the temperature all influence the performance of the air-entraining agent. The void size distribution in ordinary air-entrained concrete can show a very wide range of variation, between 10 and 3,000 micrometers ($\mu m$) or more. In such cementitious compositions, besides the small voids which are essential to cyclic freeze-thaw damage resistance, the presence of larger voids, which contribute little to the durability of the cementitious composition and could reduce the strength of the composition, has to be accepted as an unavoidable feature.

Air-entraining agents have been shown to provide resistance to freeze-thaw damage, as well as scaling damage resistance, which occurs when the surface of the hardened cementitious composition breaks away for any of a number of reasons, some of which are discussed above. However, because conventional air-entraining agents suffer from the problems discussed above, the cementitious composition industry is searching for new and better admixtures to provide the properties which are currently provided by conventional air-entraining agents.

A recent development is to use polymeric microspheres to create controlled-size voids within cementitious compositions. However, development is still ongoing to improve the function of polymeric microspheres within cementitious compositions, and to reduce the cost of including polymeric microspheres in cementitious compositions.

In order to provide appropriately sized air voids, polymeric microspheres may need to be expanded prior to incorporation into cementitious compositions. After expansion, expanded polymeric microspheres may have up to about 75 times the volume of the unexpanded microspheres. Providing cementitious composition admixtures which include expanded polymeric microspheres can be expensive, due to the high shipping cost associated with shipping an admixture which includes high-volume expanded microspheres, particularly if provided in an aqueous slurry which may include a volume of water.

What is needed is a method to provide polymeric microspheres for use in cementitious compositions and cementitious articles at a reasonable price.

Embodiments of the subject matter are disclosed with reference to the accompanying drawings and are for illustrative purposes only. The subject matter is not limited in its application to the details of construction or the arrangement of the components illustrated in the drawings. Like reference numerals are used to indicate like components, unless otherwise indicated.

Figure 1:
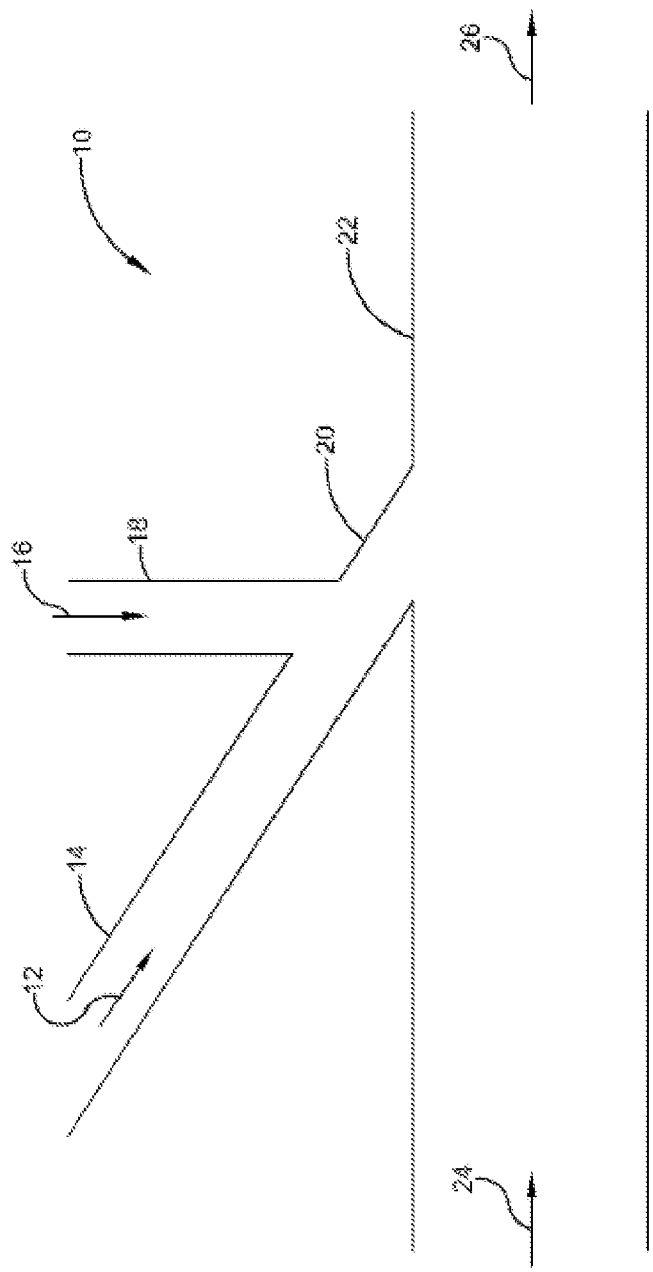
FIG. 1 is a schematic diagram of an embodiment of an apparatus for performing the subject method(s).

The expanded polymeric microspheres provide void spaces in cementitious compositions prior to final setting, and such void spaces act to increase the freeze-thaw durability of the cementitious material. Expanded polymeric microspheres introduce voids into cementitious compositions to produce a fully formed void structure in cementitious compositions which resists concrete degradation produced by water-saturated cyclic freezing and does not rely on air bubble stabilization during mixing of cementitious compositions. The freeze-thaw durability enhancement produced with the expanded polymeric microspheres is based on a physical mechanism for relieving stresses produced when water freezes in a cementitious material. In conventional practice, properly sized and spaced voids are generated in the hardened material by using chemical admixtures to stabilize the air voids entrained into a cementitious composition during mixing. In conventional cementitious compositions these chemical admixtures as a class are called air entraining agents. The present admixture utilizes expanded polymeric microspheres to form a void structure in cementitious compositions and does not require the production and/or stabilization of air entrained during the mixing process.

The use of expanded polymeric microspheres substantially eliminates some of the practical problems encountered in the current art. It also makes it possible to use some materials, i.e., low grade, high-carbon fly ash, which may be landfilled because it is considered unusable in air-entrained cementitious compositions without further treatment. This results in cement savings, and therefore economic savings. As the voids "created" by this approach are much smaller than those obtained by conventional air-entraining agents, the volume of expanded polymeric microspheres that is required to achieve the desired durability is also much lower than in conventional air entrained cementitious compositions. Therefore, a higher compressive strength can be achieved with the present admixtures and methods at the same level of protection against freezing and thawing damage. Consequently, the most expensive component used to achieve strength, i.e., cement, can be saved.

The expandable polymeric microspheres may be comprised of a polymer that is at least one of polyethylene, polypropylene, polymethyl methacrylate, poly-o-chlorostyrene, polyvinyl chloride, polyvinylidene chloride, polyacrylonitrile, polymethacrylonitrile, polystyrene, and copolymers thereof, such as copolymers of vinylidene chloride-acrylonitrile, polyacrylonitrile-copolymethacrylonitrile, polyvinylidene chloride-polyacrylonitrile, or vinyl chloride-vinylidene chloride, and the like. As the microspheres are composed of polymers, the wall may be flexible, such that it moves in response to pressure. The material from which the microspheres are to be made, therefore, may be flexible, and, in certain embodiments, resistant to the alkaline environment of cementitious compositions. Without limitation, suitable expandable polymeric microspheres are available from Eka Chemicals Inc., an Akzo Nobel company (Duluth, Ga.), under the trade name EXPANCEL®. Non-limiting examples of suitable EXPANCEL® polymeric microspheres include expanded polymeric microspheres having densities in the range of from about 0.015 g/cm$^3$ to about 0.025 g/cm$^3$ and sizes in the range of from about 20 µm to about 80 µm.

In certain embodiments, the unexpanded, expandable polymeric microspheres may have an average diameter of about 100 µm or less, in certain embodiments about 50 µm or less, in certain embodiments about 24 µm or less, in certain embodiments about 16 µm or less, in certain embodiments about 15 µm or less, in certain embodiments about 10 µm or less, and in other embodiments about 9 µm or less. In certain embodiments, the average diameter of the unexpanded polymeric microspheres may be from about 10 µm to about 16 µm, in certain embodiments from about 6 µm to about 9 µm, in certain embodiments from about 3 µm to about 6 µm, in certain embodiments from about 9 µm to about 15 µm, and in other embodiments from about 10 µm to about 24 µm. The polymeric microspheres may have a hollow core and compressible wall. The interior portion of the polymeric microspheres comprises a void cavity or cavities that may contain gas (gas filled) or liquid (liquid filled).

In certain embodiments, the expanded, expandable polymeric microspheres may have an average diameter of about 200 to about 900 µm, in certain embodiments, about 40 to about 216 µm, in certain embodiments about 36 to about 135 µm, in certain embodiments about 24 to about 81 µm, and in certain embodiments about 12 to about 54 µm.

It has been found that the smaller the diameter of the expandable polymeric microspheres, the smaller the amount of the microspheres that is required to achieve the desired freeze-thaw damage resistance in cementitious compositions. This is beneficial from a performance perspective, in that a smaller decrease in compressive strength occurs by the addition of the microspheres, as well as an economic perspective, since a smaller amount of spheres is required. Similarly, the wall thickness of the polymeric microspheres may be optimized to minimize material cost, but to ensure that the wall thickness is adequate to resist damage and/or fracture during mixing, placing, consolidating and finishing processes of the cementitious composition.

A method of expanding expandable polymeric microspheres is provided, comprising contacting an aqueous slurry comprising unexpanded, expandable polymeric microspheres with steam proximate to and/or during manufacture of a cementitious composition or cementitious article, wherein the aqueous slurry optionally further comprises an admixture for the cementitious composition or article. In certain embodiments, the method may comprise contacting an aqueous slurry comprising unexpanded, expandable polymeric microspheres with steam in-situ during manufacture of a cementitious composition or article.

A method of manufacturing a cementitious composition or cementitious article is also provided, comprising: (i) contacting an aqueous slurry of unexpanded, expandable polymeric microspheres with steam proximate to and/or during said manufacturing of the cementitious composition or article to create expanded polymeric microspheres; (ii) optionally pre-wetting the expanded polymeric microspheres; and (iii) incorporating the expanded polymeric microspheres into the cementitious composition or article, wherein the aqueous slurry optionally further comprises an admixture for the cementitious composition or article.

Figure 3:
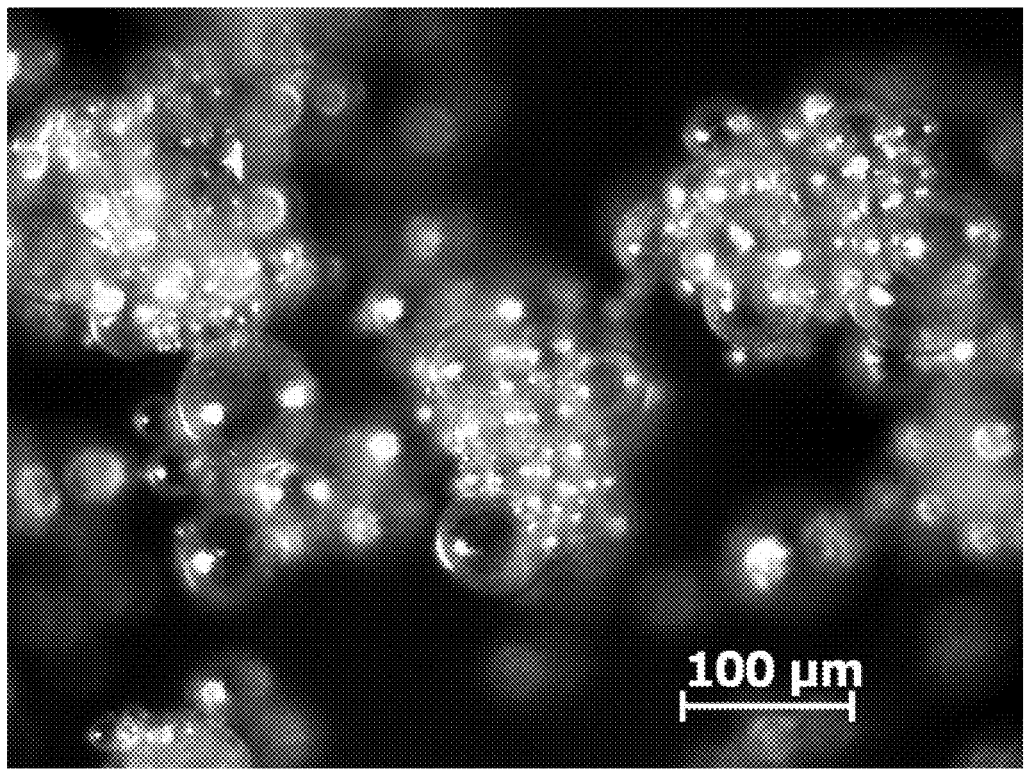
FIG. 3 is a photograph of expanded microspheres containing 85% moisture.

The process of "contacting an aqueous slurry comprising unexpanded, expandable polymeric microspheres with steam proximate to and/or during manufacture of a cementitious composition or cementitious article", may include at least one of: (i) contacting the aqueous slurry comprising the unexpanded, expandable polymeric microspheres with steam immediately prior to introducing, such as by injecting, the aqueous slurry into a feed water stream being fed into a cementitious composition during manufacture of the cementitious composition or article; or (ii) contacting the aqueous slurry comprising the unexpanded, expandable polymeric microspheres with steam to expand the expandable polymeric microspheres and quenching the expanded expandable polymeric microspheres into water at a cementitious composition or article manufacturing facility, and reserving the quenched, expanded microsphere-containing aqueous slurry for introduction into a cementitious composition or article manufactured at the facility. FIG. 3 is a photograph of expanded, expandable polymeric microspheres after being contacted with steam in order to expand the expandable polymeric microspheres. As used herein, "at a cementitious composition or article manufacturing facility" means that expansion of the unexpanded, expandable polymeric microspheres occurs at the same facility or at an adjacent or proximate facility where the cementitious composition or article is manufactured.

Figure 4:
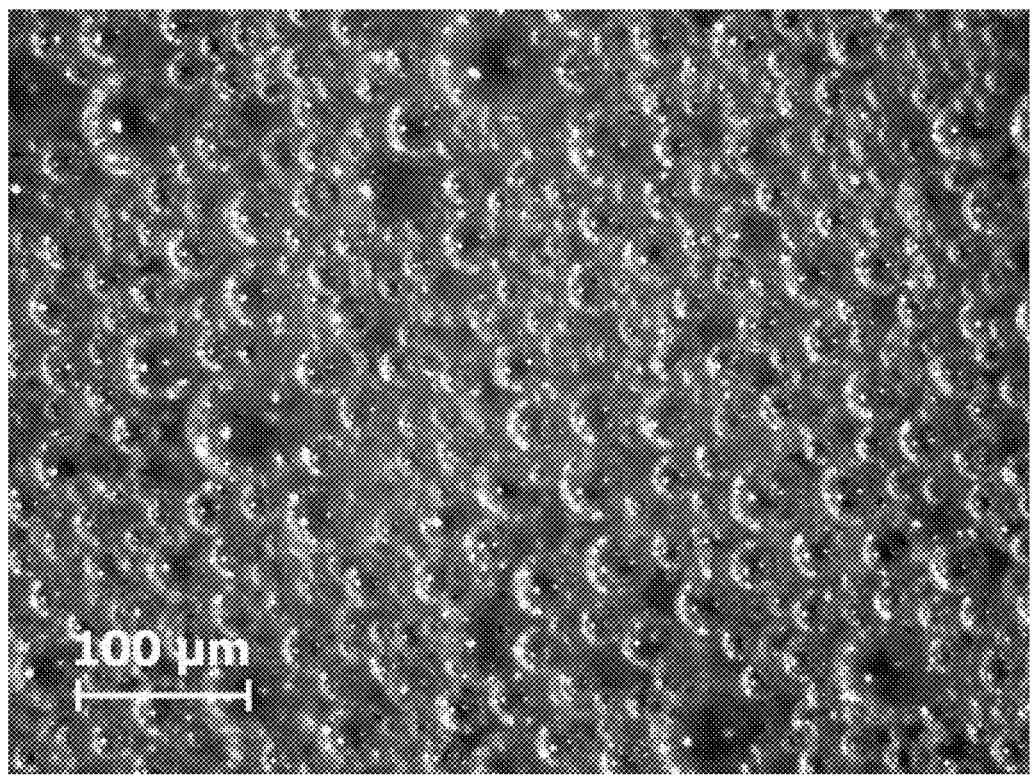
FIG. 4 is a photograph of expanded microspheres dispersed in water.

In certain embodiments, pre-wetting the expanded polymeric microspheres may comprise dispersing the expanded polymeric microspheres in liquid, optionally wherein the liquid comprises water. The pre-wetted expanded polymeric microspheres may be mixed with cement, water and other cementitious mixture components in forming the cementitious composition. FIG. 4 is a photograph of expanded polymeric microspheres dispersed in water.

In certain embodiments, pre-wetting the expanded polymeric microspheres may comprise adding the expanded polymeric microspheres and a liquid to a mixing tank, optionally wherein the liquid comprises water. In some embodiments, the expanded polymeric microspheres may comprise from about 1% to about 60% of the total volume of all material in the mixing tank.

Figure 5:
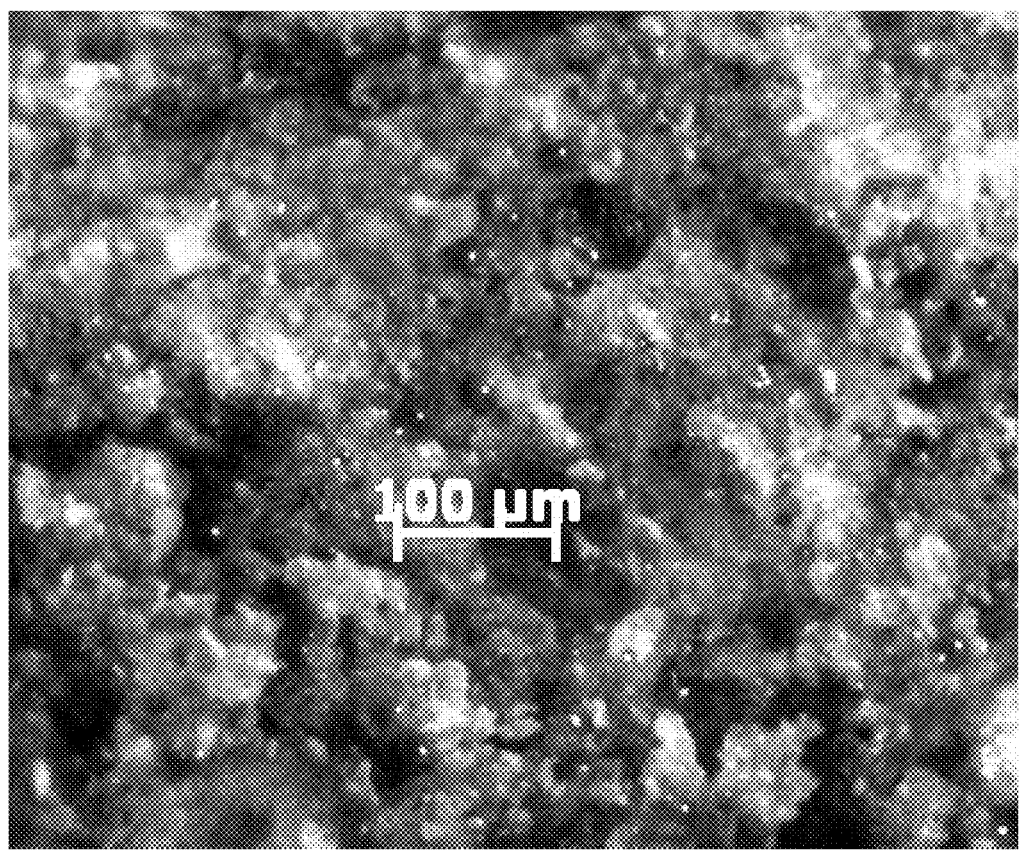
FIG. 5 is a photograph of expanded microspheres in an article of concrete.

Referring to FIG. 1, in certain embodiments, the aqueous slurry 12 comprising unexpanded, expandable polymeric microspheres is fed through a first conduit 14, while at the same time steam 16 is fed through a second conduit 18. The first 14 and second 18 conduits meet 20 immediately prior to feeding into a third conduit 22, which contains feed water 24 flowing 26 into a cementitious composition mixture. The meeting of the first and second conduits results in rapid heating of the unexpanded, expandable polymeric microspheres, causing the microspheres to expand. The expanded microspheres are then quenched by the feed water flowing through the third conduit 22, which allows the expanded microspheres to retain their size upon introduction into the cementitious composition mixture. In certain embodiments, the third conduit 22 may be flowing 26 into a reservoir vessel (not shown) and reserved for later introduction into a cementitious composition. In an alternative embodiment, the third conduit 22 may be eliminated, and the expanded microspheres may be introduced directly into an on-site reservoir vessel (not shown) after being contacted by the steam in the second conduit 18, and reserved for later introduction into a cementitious composition. FIG. 5 is a photograph of expanded polymeric microspheres in an article of concrete. In certain embodiments, the expanded microspheres may have a volume which is up to about 75 times larger than their original, unexpanded volume.

Figure 2:
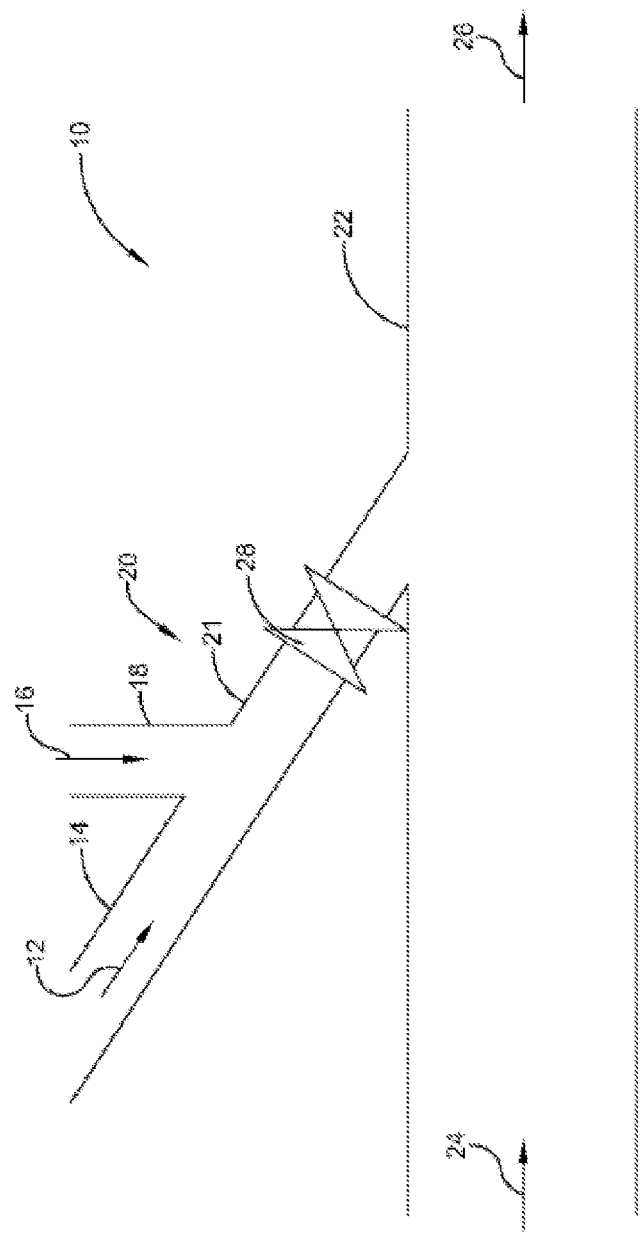
FIG. 2 is a schematic diagram of an embodiment of an apparatus for performing the subject method(s).

Referring to FIG. 2, in certain embodiments, the meeting 20 of the first 14 and second 18 conduits may comprise a fourth conduit 21. The fourth conduit 21 may include a back pressure generator 28, such as a flow control valve or a flow restriction device, such as an orifice nozzle. The back pressure generator 28 is capable of restricting and/or controlling the flow of the mixture of the aqueous slurry 12 and the steam 16 in order to ensure that the mixture achieves the proper pressure and temperature required to adequately expand the expandable microspheres in the aqueous slurry 12. In certain embodiments, the back pressure generator 28 may also at least partially prevent backflow of the feed water 24 from the third conduit 22.

In certain embodiments, the expanded polymeric microspheres, and/or an admixture containing them, may be prepared using an apparatus comprising: (a) a steam generator or other source of steam; (b) a steam conduit in fluid communication with the steam generator or other steam source; (c) a fluid material conduit in fluid communication with a source of a fluid material, wherein the fluid material comprises unexpanded, expandable polymeric microspheres; (d) a treatment zone in fluid communication with the steam generator or other steam source via the steam conduit, and with the fluid material conduit, such that the fluid material is contacted by steam within the treatment zone; and (e) a back pressure generator in fluid communication with the treatment zone, capable of increasing pressure in the treatment zone, which results in expansion of the expandable polymeric microspheres when the fluid material exits the treatment zone.

In one embodiment, a fluid material including water and the unexpanded, expandable polymeric microspheres to be included in the cementitious composition, cementitious article, or an admixture therefor, is contacted with steam within the treatment zone, such that the unexpanded, expandable polymeric microspheres are subjected to increased temperature and pressure, which results in pre-expansion of the expandable polymeric microspheres. Upon exiting the treatment zone, optionally via the back pressure generator, the expandable polymeric microspheres experience a pressure drop equal to the difference between the pressure in the treatment zone and the pressure in the environment outside the treatment zone. This sudden decrease in pressure results in rapid expansion of the expandable polymeric microspheres.

The back pressure generator is capable of restricting and/or controlling the flow of the fluid material and steam through the treatment zone, to ensure that the temperature and pressure within the treatment zone are sufficient to provide enough of a pressure drop to allow the expandable polymeric microspheres to expand to a desired degree upon exiting the back pressure generator. The back pressure generator may comprise, for example, a flow control valve or a flow restriction device, such as an orifice nozzle.

In certain embodiments, the temperature inside the treatment zone may be from about 105° C. (221° F.) to about 145° C. (293° F.), in certain embodiments from about 135° C. (275° F.) to about 145° C. (293° F.). In certain embodiments, the pressure inside the treatment zone may be from about 120 kPa (17.4 psi) to about 420 kPa (60.9 psi), in certain embodiments from about 315 kPa (45.7 psi) to about 420 kPa (60.9 psi).

The fluid material comprising the expanded, expandable polymeric microspheres may be added to or mixed with process water or other liquid admixtures, and then incorporated into the cementitious composition or article. Alternatively, the fluid material comprising the expanded, expandable polymeric microspheres may be incorporated directly into a cementitious composition (before or during mixing of the cementitious composition components) without first adding the treated fluid material to process water or other liquid admixtures.

The present methods may be performed on-site at cementitious composition manufacturing facilities, such as ready-mix concrete plants. Such facilities may include storage areas for cement, water, and other components to be added to the cementitious compositions being produced, such as aggregate and/or cementitious composition admixtures. At the facilities, the various components of cementitious compositions, such as cement, water, aggregate, and/or admixtures are mixed together to form a cementitious composition. The mixing may be performed on a mixing truck, such as a concrete mixing truck. Once the components are mixed, the cementitious composition may be transported to a job site, where the composition is placed and allowed to harden. The cementitious composition may also be utilized to manufacture cementitious articles, such as concrete block or concrete pavers, on-site at the cementitious composition manufacturing facilities or at another facility.

After expansion and pre-wetting, the expanded polymeric microspheres may then be introduced directly into the cementitious composition mixture during manufacture, such as being provided to a central mixer in the facility, or may be temporarily retained in one or more reservoirs or batch tanks. The number and capacity of the reservoirs or batch tanks may be related to the productivity of the expansion apparatus and/or the cycle time of the batching of cementitious composition components during manufacture. In certain embodiments, such as ready-mix concrete manufacture, the expansion and introduction into a batch tank of an amount of expanded polymeric microspheres needed for one concrete mixer truck may be timed to be completed in less than or equal to the time needed for batching the truck with all of the cementitious composition components. At least one batch tank may be in a filling mode while another batch tank is discharging its contents of a dispersion of expanded polymeric microspheres or a liquid admixture containing the expanded polymeric microspheres into the cementitious mixture in the truck.

In certain embodiments, the present methods allow for an aqueous slurry of expandable polymeric microspheres and/or an admixture comprising unexpanded, expandable polymeric microspheres to be shipped to cementitious composition manufacturing facilities at minimal cost. Once the aqueous slurry and/or admixture containing the unexpanded, expandable polymeric microspheres arrives at such a facility, the expandable polymeric microspheres may be expanded on-site. As compared with shipping slurries and/or admixtures which contain expanded expandable polymeric microspheres, which may have a volume of up to 75 times greater than unexpanded microspheres, shipping slurries and/or admixtures which contain unexpanded expandable microspheres drastically reduces shipping costs, which could equal or exceed the actual cost of the admixture. Furthermore, other logistical costs, such as storage, may also be reduced.

In certain embodiments, a cementitious composition comprising 1.5% by volume, based on the total volume of the cementitious composition, of expanded expandable polymeric microspheres may have a 30% higher 28-day compressive strength as compared to a cementitious composition comprising a conventional air-entraining agent, yet can also pass ASTM C 666, which is incorporated herein by reference. ASTM C-666 is used to test the freeze-thaw damage resistance of cementitious compositions.

The hydraulic cement may be a Portland cement, a calcium aluminate cement, a magnesium phosphate cement, a magnesium potassium phosphate cement, a calcium sulfoaluminate cement or any other suitable hydraulic binder. Aggregate may be included in the cementitious composition. The aggregate can be silica, quartz, sand, crushed marble, glass spheres, granite, limestone, calcite, feldspar, alluvial sands, any other durable aggregate, and mixtures thereof.

In certain embodiments, the amount of expanded, expandable polymeric microspheres to be included in the cementitious composition (which may comprise a cementitious article), delivered via the admixtures and/or methods described herein, may be from about 0.002 to about 0.06 percent by weight, based on the total weight of the cementitious composition. In other embodiments, the amount of expandable polymeric microspheres to be included in the cementitious composition, delivered via the subject admixtures or methods, may be from about 0.005 to about 0.04 percent by weight, based on the total weight of the cementitious composition. In further embodiments, the amount of expandable polymeric microspheres to be included in the cementitious composition, delivered via the subject admixtures or methods, may be from about 0.008 to about 0.03 percent by weight, based on the total weight of the cementitious composition.

In certain embodiments, the amount of expanded, expandable polymeric microspheres to be included in the cementitious composition, delivered via the admixtures and/or methods described herein, may be from about 0.2 to about 4 percent by volume, based on the total volume of the cementitious composition. In certain embodiments, the amount of expanded, expandable polymeric microspheres to be included in the cementitious composition, delivered via the subject admixtures or methods, may be from about 0.25 to about 4 percent by volume, based on the total volume of the cementitious composition. In certain embodiments, the amount of expanded, expandable polymeric microspheres to be included in the cementitious composition, delivered via the subject admixtures or methods, may be from about 0.4 to about 4 percent by volume, based on the total volume of the cementitious composition. In certain embodiments, the amount of expanded, expandable polymeric microspheres to be included in the cementitious composition, delivered via the subject admixtures or methods, may be from about 0.25 to about 3 percent by volume, based on the total volume of the cementitious composition. In certain embodiments, the amount of expanded, expandable polymeric microspheres to be included in the cementitious composition, delivered via the subject admixtures or methods, may be from about 0.5 to about 3 percent by volume, based on the total volume of the cementitious composition.

A non-limiting example of an apparatus suitable for expanding the expandable polymeric microspheres according to the present methods comprises: (a) a steam generator having a power output of less than or equal to about 6 boiler horsepower; (b) a steam conduit in fluid communication with the steam generator; (c) a fluid material conduit in fluid communication with a source of a fluid material, wherein the fluid material comprises unexpanded, expandable polymeric microspheres; (d) a treatment zone in fluid communication with the steam generator via the steam conduit, and with the fluid material conduit, such that the fluid material is contacted by steam within the treatment zone; and e. a back pressure generator in fluid communication with the treatment zone, capable of increasing pressure in the treatment zone, which results in expansion of the expandable polymeric microspheres when the fluid material exits the treatment zone. The apparatus may have a footprint which allows the apparatus to be placed inside a manufacturing facility which uses the expanded expandable polymeric microspheres in products of manufacture, such as cementitious compositions or cementitious articles, without substantially adversely affecting production of the products of manufacture.

The following examples illustrate the performance of cementitious compositions made using embodiments of the present method(s), and should not be construed to limit the present subject matter in any manner.

EXAMPLE 1

A cementitious composition was prepared in a central mixer at a cementitious composition manufacturing facility. The cementitious composition included 1,833 lbs. of cement, 3,900 lbs. of sand, 3,171 lbs. of #57 stone, 2,154 lbs. #8 stone and 917 lbs. of water. The volume of the cementitious composition was about 3 yd$^3$. The cementitious composition included 2,713 mL of Pozzolith® 80 water reducing admixture, available from BASF Construction Chemicals, Cleveland, Ohio, 3,798 mL of Glenium® 7500 high-range water reducing admixture, also available from BASF Construction Chemicals, and 814 mL tributylphosphate defoaming admixture. After mixing in the central mixer was complete, the cementitious composition was transferred to a concrete mixing truck.

Once the cementitious composition was inside the concrete mixing truck, 2% by volume of the cementitious composition of expanded polymeric microspheres, expanded via the present method(s), having a density of about 0.025 g/cm$^3$ and a size of about 40 μm were added into the top of the mixing truck. The mixing truck mixed the cementitious composition at high speed for 2-3 minutes, and a sample was taken from the top of the mixing truck. After about 20 minutes of mixing at low speed, a second sample was taken from the top of the mixing truck. After a total of about 40 minutes of mixing at low speed, a third sample was taken from the top of the mixing truck. After a total of about 60 minutes, a fourth sample was taken from the top of the mixing truck.

The samples were very fluid, having an average initial slump of about 28.75 inches and average air content of 1.8%. Because the samples were so fluid, and also because they were taken from the top of the mixing truck, there were more microspheres in the samples than were present throughout the cementitious composition on average. Testing of the samples to determine the amount of microspheres showed that the samples had an average microsphere content of about 2.5% by volume of the cementitious composition. The samples passed the ASTM C666 test with an average durability factor of about 90.

EXAMPLE 2

A cementitious composition was prepared in a central mixer at a cementitious composition manufacturing facility. The cementitious composition included 760 lbs. of water, 1,690 lbs. of cement, 4,020 lbs. of sand, 3,020 lbs. of #57 stone, and 2,000 lbs. #8 stone. The volume of the cementitious composition was about 3 yd$^3$. The cementitious composition also included 1,501 mL of Glenium® 7500 high-range water reducing admixture and 750 mL tributylphosphate ("TBP") defoaming admixture.

Prior to adding other ingredients to the central mixture, 1.5% by volume of the cementitious composition of expanded polymeric microspheres, expanded via the present method(s), having a density of 0.025 g/cm$^3$ and a size of about 40 μm were added to the central mixer manually in an aqueous slurry. The TBP was added to the central mixture manually with the expanded polymeric microspheres. After addition of the expanded polymeric microspheres and the TBP, the other ingredients of the cementitious composition were added to the central mixer automatically using the manufacturing facility's automated dispensing system. The dust collector for the central mixer was off while the expanded polymeric microspheres and the TBP were added to the central mixer, and was not turned on until 30 second after mixing of the cementitious composition began.

A first sample of the cementitious composition was taken as soon as mixing was completed. The first sample had a slump value of 5.00 inches and 2.1% air content, and passed the ASTM C666 test with a durability factor of 95. A second sample of the cementitious composition was taken 30 minutes after mixing was completed. The second sampled had a slump value of 3.75 inches and 2.5% air content, and passed the ASTM C666 test with a durability factor of 83.

EXAMPLE 3

A cementitious composition was prepared in a central mixer at a cementitious composition manufacturing facility. The cementitious composition included 1,520 lbs. of water, 3,380 lbs. of cement, 8,040 lbs. of sand, 6,040 lbs. of #57 stone, and 4,000 lbs. #8 stone. The volume of the cementitious composition was about 6 yd$^3$. The cementitious composition included 4,002 mL of Glenium® 7500 high-range water reducing admixture and 1,501 mL tributylphosphate defoaming admixture.

Prior to adding other ingredients to the central mixture, 1.5% by volume of the cementitious composition of expanded polymeric microspheres, expanded via the present method(s), having a density of 0.025 g/cm$^3$ and a size of about 40 μm were added to the central mixer manually in an aqueous slurry. The TBP was added to the central mixture manually with the expanded polymeric microspheres. After addition of the expanded polymeric microspheres and the TBP, the other ingredients of the cementitious composition were added to the central mixer automatically using the manufacturing facility's automated dispensing system. The dust collector for the central mixer was off while the expanded polymeric microspheres and the TBP were added to the central mixer, and was not turned on until 30 second after mixing of the cementitious composition began.

A first sample of the cementitious composition was taken as soon as mixing was completed. The first sample had a slump value of 7.75 inches and 1.7% air content, and passed the ASTM C666 test with a durability factor of 95. A second sample of the cementitious composition was taken 30 minutes after mixing was completed. The second sample had a slump value of 7.00 inches and 2.0% air content, and passed the ASTM C666 test with a durability factor of 87.

EXAMPLE 4

A cementitious composition was prepared in a central mixer at a cementitious composition manufacturing facility. The cementitious composition included 1,204 lbs. of water, 2,780 lbs. of cement, 6,355 lbs. of sand, 5,069 lbs. of #57 stone, and 3,388 lbs. #8 stone. The volume of the cementitious composition was about 5 yd$^3$. The cementitious composition included 3.0% by volume of the cementitious composition of Pozzolith® 80 water reducing admixture and 1,500 mL tributylphosphate defoaming admixture.

Prior to adding other ingredients to the central mixture, 0.75% by volume of the cementitious composition of expanded polymeric microspheres, expanded via the present method(s), having a density of 0.025 g/cm$^3$ and a size of about 40 μm were added to the central mixer manually in an aqueous slurry. The TBP was added to the central mixture manually with the expanded polymeric microspheres. After addition of the expanded polymeric microspheres and the TBP, the other ingredients of the cementitious composition were added to the central mixer.

A sample of the cementitious composition was taken, having a slump value of 5.50 inches and 2.4% air content. The sample passed the ASTM C666 test with a durability factor of 95.

A cementitious composition made using the method(s) described herein may contain other admixtures or ingredients and should not be necessarily limited to the stated formulations. These admixtures and/or ingredients that may be added include, but are not limited to: dispersants, set and strength accelerators/enhancers, set retarders, water reducers, corrosion inhibitors, wetting agents, water soluble polymers, rheology modifying agents, water repellents, non degrading fibers, dampproofing admixtures, permeability reducers, fungicidal admixtures, germicidal admixtures, insecticide admixtures, alkali-reactivity reducer, bonding admixtures, shrinkage reducing admixtures, and any other admixture or additive suitable for use in cementitious compositions. The admixtures and cementitious compositions described herein need not contain any of the foregoing components, but may contain any number of the foregoing components.

Aggregate can be included in the cementitious composition to provide mortars which include fine aggregate, and concretes which include fine and coarse aggregates. The fine aggregates are materials that almost entirely pass through a Number 4 sieve (ASTM C 125 and ASTM C 33), such as silica sand. The coarse aggregates are materials that are predominantly retained on a Number 4 sieve (ASTM C 125 and ASTM C 33), such as silica, quartz, crushed marble, glass spheres, granite, limestone, calcite, feldspar, alluvial sands, sands or any other durable aggregate, and mixtures thereof.

A pozzolan is a siliceous or aluminosiliceous material that possesses little or no cementitious value but will, in the presence of water and in finely divided form, chemically react with the calcium hydroxide produced during the hydration of Portland cement to form materials with cementitious properties. Diatomaceous earth, opaline cherts, clays, shales, fly ash, slag, silica fume, volcanic tuffs and pumicites are some of the known pozzolans. Certain ground granulated blast-furnace slags and high calcium fly ashes possess both pozzolanic and cementitious properties. Natural pozzolan is a term of art used to define the pozzolans that occur in nature, such as volcanic tuffs, pumices, trasses, diatomaceous earths, opaline, cherts, and some shales. Nominally inert materials can also include finely divided raw quartz, dolomites, limestones, marble, granite, and others. Fly ash is defined in ASTM C618.

If used, silica fume can be uncompacted or can be partially compacted or added as a slurry. Silica fume additionally reacts with the hydration byproducts of the cement binder, which provides for increased strength of the finished articles and decreases the permeability of the finished articles. The silica fume, or other pozzolans such as fly ash or calcined clay such as metakaolin, can be added to the cementitious wet cast mixture in an amount from about 5% to about 70% based on the weight of cementitious material.

A dispersant if used can be any suitable dispersant such as lignosulfonates, beta naphthalene sulfonates, sulfonated melamine formaldehyde condensates, polyaspartates, polycarboxylates with and without polyether units, naphthalene sulfonate formaldehyde condensate resins, or oligomeric dispersants.

Polycarboxylate dispersants can be used, by which is meant a dispersant having a carbon backbone with pendant side chains, wherein at least a portion of the side chains are attached to the backbone through a carboxyl group, an ether group, or an amide or imide group. The term dispersant is also meant to include those chemicals that also function as a plasticizer, high range water reducer, fluidizer, antiflocculating agent, or superplasticizer for cementitious compositions.

The term oligomeric dispersant refers to oligomers that are a reaction product of: component A, optionally component B, and component C; wherein each component A is independently a nonpolymeric, functional moiety that adsorbs onto a cementitious particle; wherein component B is an optional moiety, where if present, each component B is independently a nonpolymeric moiety that is disposed between the component A moiety and the component C moiety; and wherein component C is at least one moiety that is a linear or branched water soluble, nonionic polymer substantially non-adsorbing to cement particles. Oligomeric dispersants are disclosed in U.S. Pat. Nos. 6,133,347, 6,492,461, and No. 6,451,881.

Set and strength accelerators/enhancers that can be used include, but are not limited to: a nitrate salt of an alkali metal, alkaline earth metal, or aluminum; a nitrite salt of an alkali metal, alkaline earth metal, or aluminum; a thiocyanate of an alkali metal, alkaline earth metal or aluminum; an alkanolamine; a thiosulphate of an alkali metal, alkaline earth metal, or aluminum; a hydroxide of an alkali metal, alkaline earth metal, or aluminum; a carboxylic acid salt of an alkali metal, alkaline earth metal, or aluminum (preferably calcium formate); a polyhydroxylalkylamine; and/or a halide salt of an alkali metal or alkaline earth metal (preferably bromide).

The salts of nitric acid have the general formula $M(NO_3)_a$ where M is an alkali metal, or an alkaline earth metal or aluminum, and where a is 1 for alkali metal salts, 2 for alkaline earth salts, and 3 for aluminum salts. Preferred are nitric acid salts of Na, K, Mg, Ca and Al.

Nitrite salts have the general formula $M(NO_2)_a$ where M is an alkali metal, or an alkaline earth metal or aluminum, and where a is 1 for alkali metal salts, 2 for alkaline earth salts, and 3 for aluminum salts. Preferred are nitric acid salts of Na, K, Mg, Ca and Al.

The salts of the thiocyanic acid have the general formula $M(SCN)_b$, where M is an alkali metal, or an alkaline earth metal or aluminum, and where b is 1 for alkali metal salts, 2 for alkaline earth salts and 3 for aluminum salts. These salts are variously known as sulfocyanates, sulfocyanides, rhodanates or rhodanide salts. Preferred are thiocyanic acid salts of Na, K, Mg, Ca and Al.

Alkanolamine is a generic term for a group of compounds in which trivalent nitrogen is attached directly to a carbon atom of an alkyl alcohol. A representative formula is $N[H]_c[(CH_2)_d CHRCH_2R]_e$, where R is independently H or OH, c is 3-e, d is 0 to about 4 and e is 1 to about 3. Examples include, but are not limited to, are monoethanoalamine, diethanolamine, triethanolamine and triisopropanolamine.

The thiosulfate salts have the general formula $M_f(S_2O_3)_g$ where M is alkali metal or an alkaline earth metal or aluminum, and f is 1 or 2 and g is 1, 2 or 3, depending on the valencies of the M metal elements. Preferred are thiosulfate acid salts of Na, K, Mg, Ca and Al.

The carboxylic acid salts have the general formula RCOOM wherein R is H or $C_1$ to about $C_{10}$ alkyl, and M is alkali metal or an alkaline earth metal or aluminum. Preferred are carboxylic acid salts of Na, K, Mg, Ca and Al. An example of carboxylic acid salt is calcium formate.

A polyhydroxylalkylamine may have the general formula:

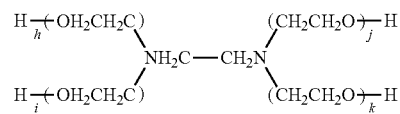

wherein h is 1 to 3, i is 1 to 3, j is 1 to 3, and k is 0 to 3. A preferred polyhydroxyalkylamine is tetrahydroxyethylethylenediamine.

Set retarding, or also known as delayed-setting or hydration control, admixtures are used to retard, delay, or slow the rate of setting of cementitious compositions. Set retarders are used to offset the accelerating effect of hot weather on the setting of cementitious compositions, or delay the initial set of cementitious compositions when difficult conditions of placement occur, or problems of delivery to the job site, or to allow time for special finishing processes. Most set retarders also act as low level water reducers and can also be used to entrain some air into cementitious compositions. Lignosulfonates, hydroxylated carboxylic acids, borax, gluconic, tartaric and other organic acids and their corresponding salts, phosphonates, certain carbohydrates such as sugars, polysaccharides and sugar-acids and mixtures thereof can be used as retarding admixtures.

Corrosion inhibitors serve to protect embedded reinforcing steel from corrosion. The high alkaline nature of cementitious compositions causes a passive and non-corroding protective oxide film to form on the steel. However, carbonation or the presence of chloride ions from deicers or seawater, together with oxygen can destroy or penetrate the film and result in corrosion. Corrosion-inhibiting admixtures chemically slow this corrosion reaction. The materials most commonly used to inhibit corrosion are calcium nitrite, sodium nitrite, sodium benzoate, certain phosphates or fluorosilicates, fluoroaluminates, amines, organic based water repelling agents, and related chemicals.

In the construction field, many methods of protecting cementitious compositions from tensile stresses and subsequent cracking have been developed through the years. One modern method involves distributing fibers throughout a fresh cementitious mixture. Upon hardening, this cementitious composition is referred to as fiber-reinforced cement. Fibers can be made of zirconium materials, carbon, steel, fiberglass, or synthetic materials, e.g., polypropylene, nylon, polyethylene, polyester, rayon, high-strength aramid, or mixtures thereof.

Dampproofing admixtures reduce the permeability of concrete that has low cement contents, high water-cement ratios, or a deficiency of fines in the aggregate portion. These admixtures retard moisture penetration into wet concrete and include certain soaps, stearates, and petroleum products.

Permeability reducers are used to reduce the rate at which water under pressure is transmitted through cementitious compositions. Silica fume, fly ash, ground slag, metakaolin, natural pozzolans, water reducers, and latex can be employed to decrease the permeability of the cementitious compositions.

Bacteria and fungal growth on or in hardened cementitious compositions may be partially controlled through the use of fungicidal, germicidal, and insecticidal admixtures. The most effective materials for these purposes are polyhalogenated phenols, dialdrin emulsions, and copper compounds.

Coloring admixtures are usually composed of pigments, either organic such as phthalocyanine or inorganic pigments such as metal-containing pigments that comprise, but are not limited to metal oxides and others, and can include, but are not limited to, iron oxide containing pigments, chromium oxide, aluminum oxide, lead chromate, titanium oxide, zinc white, zinc oxide, zinc sulfide, lead white, iron manganese black, cobalt green, manganese blue, manganese violet, cadmium sulfoselenide, chromium orange, nickel titanium yellow, chromium titanium yellow, cadmium sulfide, zinc yellow, ultramarine blue and cobalt blue.

Alkali-reactivity reducers can reduce the alkali-aggregate reaction and limit the disruptive expansion forces that this reaction can produce in hardened cementitious compositions. Pozzolans (fly ash, silica fume), blast-furnace slag, salts of lithium and barium are especially effective.

The shrinkage reducing agent which can be used comprises but is not limited to $RO(AO)_{1-10}H$, wherein R is a $C_{1-5}$ alkyl or $C_{5-6}$ cycloalkyl radical and A is a $C_{2-3}$ alkylene radical, alkali metal sulfate, alkaline earth metal sulfates, alkaline earth oxides, preferably sodium sulfate and calcium oxide.

The above listings of additional admixtures and additives are illustrative and not exhaustive or limiting.

It will be understood that the embodiments described herein are merely exemplary, and that one skilled in the art may make variations and modifications without departing from the spirit and scope of the invention. All such variations and modifications are intended to be included within the scope of the invention as described hereinabove. Further, all embodiments disclosed are not necessarily in the alternative, as various embodiments of the invention may be combined to provide the desired result.

What is claimed is:

1. A method of expanding expandable polymeric microspheres comprising contacting an aqueous slurry comprising unexpanded, expandable polymeric microspheres with steam proximate to and/or during manufacture of a cementitious composition, wherein the aqueous slurry further comprises an admixture for the cementitious composition, and wherein the method further comprises adding the admixture for the cementitious composition to the aqueous slurry prior to contacting the aqueous slurry with steam.

2. The method of claim 1, wherein the method comprises contacting the aqueous slurry with steam in-situ during manufacture of a cementitious composition.

3. The method of claim 2, wherein said contacting the aqueous slurry with steam in-situ during manufacture of a cementitious composition comprises contacting the aqueous slurry with steam prior to introducing the aqueous slurry into a feed water stream being fed into a cementitious composition during manufacture of the cementitious composition.

4. The method of claim 3, wherein the flow of the aqueous slurry into the feed water stream is restricted and/or controlled.

5. The method of claim 3, wherein the feed water stream is fed into a cementitious composition mixing truck.

6. The method of claim 1, wherein said contacting the aqueous slurry with steam proximate to and/or during manufacture of a cementitious composition comprises contacting the aqueous slurry with steam to expand the expandable polymeric microspheres and quenching the expanded expandable polymeric microspheres into water at a cementitious composition manufacturing facility, and reserving the aqueous slurry for introduction into a cementitious composition manufactured at the facility.

7. The method of claim 6, wherein the quenched, expanded microsphere-containing aqueous slurry is reserved in a reserve tank.

8. The method of claim 6, wherein prior to said quenching the expanded expandable polymeric microspheres into water, the flow of the aqueous slurry is restricted and/or controlled.

9. A method of manufacturing a cementitious composition or cementitious article comprising the composition, the method comprising: (i) contacting an aqueous slurry of unexpanded, expandable polymeric microspheres with steam proximate to and/or during said manufacturing of the cementitious composition to create expanded polymeric microspheres;
(ii) optionally pre-wetting the expanded polymeric microspheres; and (iii) incorporating the expanded polymeric microspheres into the cementitious composition, wherein the aqueous slurry further comprises an admixture for the cementitious composition, and wherein the method further comprises adding the admixture for the cementitious composition to the aqueous slurry prior to contacting the aqueous slurry with steam.

10. The method of claim 9, wherein the method comprises contacting the aqueous slurry with steam in-situ during manufacture of a cementitious composition.

11. The method of claim 9, wherein said pre-wetting the expanded polymeric microspheres comprises dispersing the expanded polymeric microspheres in liquid, optionally wherein the liquid comprises water.

12. The method of claim 9, wherein said pre-wetting the expanded polymeric microspheres comprises adding the expanded polymeric microspheres and a liquid to a mixing tank, optionally wherein the liquid comprises water.

13. The method of claim 12, wherein the expanded polymeric microspheres comprise from about 1% to about 60% of the total volume of all material in the mixing tank.

14. The method of claim 9, wherein after said contacting the aqueous slurry with steam, the flow of the aqueous slurry is restricted and/or controlled.

15. The method of claim 14, wherein the flow of the aqueous slurry is restricted and/or controlled by a device which generates back pressure.

16. The method of claim 15, wherein the device which generates back pressure is a valve or an orifice nozzle.

17. The method of claim 9, further comprising retaining a liquid admixture containing the pre-wetted, expanded polymeric microspheres in at least one of a plurality of reservoirs prior to introduction and mixing into the cementitious composition.

* * * * *